United States Patent
Lifshitz-Liron et al.

(10) Patent No.: US 7,247,751 B2
(45) Date of Patent: Jul. 24, 2007

(54) PROCESSES FOR PREPARING CINACALCET HYDROCHLORIDE CRYSTAL FORM I

(75) Inventors: Revital Lifshitz-Liron, Hertzlia (IL); Sharon Avhar-Maydan, Givataym (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

(21) Appl. No.: 11/439,570

(22) Filed: May 23, 2006

(65) Prior Publication Data

US 2007/0099998 A1    May 3, 2007

Related U.S. Application Data

(60) Provisional application No. 60/684,152, filed on May 23, 2005, provisional application No. 60/696,981, filed on Jul. 5, 2005, provisional application No. 60/697,111, filed on Jul. 6, 2005, provisional application No. 60/698,613, filed on Jul. 11, 2005, provisional application No. 60/701,232, filed on Jul. 20, 2005, provisional application No. 60/702,918, filed on Jul. 26, 2005, provisional application No. 60/706,910, filed on Aug. 9, 2005, provisional application No. 60/730,050, filed on Oct. 24, 2005, provisional application No. 60/732,083, filed on Oct. 31, 2005, provisional application No. 60/733,008, filed on Nov. 2, 2005, provisional application No. 60/734,669, filed on Nov. 7, 2005, provisional application No. 60/735,126, filed on Nov. 8, 2005, provisional application No. 60/738,827, filed on Nov. 21, 2005, provisional application No. 60/741,787, filed on Dec. 1, 2005, provisional application No. 60/750,910, filed on Dec. 15, 2005, provisional application No. 60/794,804, filed on Apr. 24, 2006.

(51) Int. Cl.
*C07C 211/00* (2006.01)
(52) U.S. Cl. .................................... 564/337
(58) Field of Classification Search ............... 564/337
See application file for complete search history.

(56) References Cited

U.S. PATENT DOCUMENTS

| | | | |
|---|---|---|---|
| 4,966,988 | A | 10/1990 | Schinski et al. |
| 5,648,541 | A | 7/1997 | Van Wagenen et al. |
| 6,011,068 | A | 1/2000 | Nemeth et al. |
| 6,031,003 | A | 2/2000 | Nemeth et al. |
| 6,211,244 | B1 | 4/2001 | Van Wagenen et al. |
| 6,313,146 | B1 | 11/2001 | Van Wagenen et al. |
| 2005/0147669 | A1 | 7/2005 | Lawrence et al. |

OTHER PUBLICATIONS

"Sensipar (Cinacalcet HCl) Tablets" Summary Basis of Approval of New Drug Application #21-688 By FDA, (2004).
J. Iqbal, et al. "Cinacalcet Hydrochloride" *IDrugs*, vol. 6, No. 6, p. 587-592, (2003).
L.A. Sorbera, et al. "Cinacalcet Hydrochloride" *Drugs of the Future*, vol. 27, No. 9, p. 831-836, (2002).
X. Wang, et al. "Synthesis of Cinacalcet Congeners" *Tetrahedron Letters*, vol. 45, p. 8355-8358, (2004).
Snyder, L.R. et al., *Introduction To Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.

*Primary Examiner*—Samuel Barts
(74) *Attorney, Agent, or Firm*—Kenyon & Kenyon LLP

(57) ABSTRACT

The invention provides processes for the preparation of cinacalcet hydrochloride crystalline Form I.

29 Claims, 2 Drawing Sheets

TGA thermogram of Cinacalcet HCl crystalline Form I

Illustrates an XRD diffractogram of amorphous Cinacalcet hydrochloride.

File: cinacalcet HCl MS-1188, ID: Analyst: Ayelet
Step : 0.050° Cnt Time: 1.000 Sec.
Range 2.00 - 40.00 (Deg) Cont: Scan Rate 3.00 Deg/min.

PROCESSES FOR PREPARING CINACALCET HYDROCHLORIDE CRYSTAL FORM I

RELATED APPLICATIONS

This application claims the benefit of U.S. provisional application Nos. 60/684,152, filed May 23, 2005; 60/698,613, filed Jul. 11, 2005; 60/702,918, filed Jul. 26, 2005; 60/734,669, filed Nov. 7, 2005; 60/738,827, filed Nov. 21, 2005; 60/750,910, filed Dec. 15, 2005; 60/696,981, filed Jul. 5, 2005; 60/697,111, filed Jul. 6, 2005; 60/701,232, filed Jul. 20, 2005; 60/706,910, filed Aug. 9, 2005; 60/735,126, filed Nov. 8, 2005; 60/794,804, filed Apr. 24, 2006; 60/730,050, filed Oct. 24, 2005; 60/732,083, filed Oct. 31, 2005; 60/733,008, filed Nov. 2, 2005; and 60/741,787, filed Dec. 1, 2005, hereby incorporated by reference in their entirety.

FIELD OF THE INVENTION

The present invention is directed to a process of preparing a crystalline form of (R)-α-methyl-N-[3-[3-(trifluoromethyl)phenyl]propyl]-1-naphthalenemethane amine hydrochloride.

BACKGROUND OF THE INVENTION (R)-α-methyl-N-[3-[3-(trifluoromethyl)phenyl]propyl]-1-naphthalenemethane amine (herein "Cinacalcet" or "CNC") has a CAS number of 226256-56-0, a formula of $C_{22}H_{22}F_3N$ and the following structure:

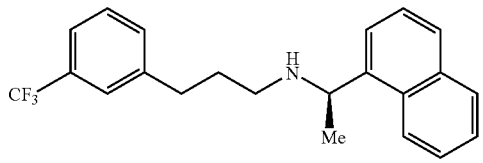

Cinacalcet is the free base form of Cinacalcet hydrochloride (herein "CNC-HCl"), which has a CAS number of 364782-34-3 and the following structure:

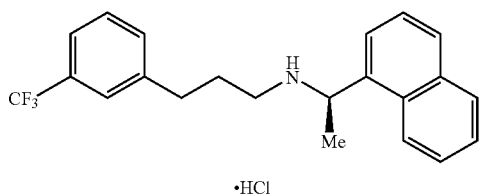

CNC-HCl is marketed as SENSIPAR™, and was the first drug in a class of compounds known as calcimimetics to be approved by the FDA. Calcimimetics are a class of orally active, small molecules that decrease the secretion of parathyroid hormone ("PTH") by activating calcium receptors. The secretion of PTH is normally regulated by the calcium-sensing receptor. Calcimimetics increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, which can result in bone pain, fractures, and an increased risk for cardiovascular death. As a calcimimetic, CNC-HCl is approved for the treatment of secondary hyperparathyroidism in patients with chronic kidney disease, who are on dialysis. Treatment with CNC-HCl lowers serum levels of PTH as well as the calcium/phosphorus ion product, a measure of the amount of calcium and phosphorus in the blood.

Inorganic ion receptor-active molecules, especially calcium receptor-active molecules, such as those having the general structure of Cinacalcet, are disclosed in U.S. Pat. No. 6,011,068. U.S. Pat. No. 6,211,244 discloses calcium receptor-active compounds related to Cinacalcet and methods of making such compounds. Cinacalcet and its enantiomer may be produced by various methods, using the processes disclosed in U.S. Pat. No. 6,211,244; *DRUGS OF THE FUTURE*, 27 (9), 831 (2002); U.S. Pat. Nos. 5,648,541, 4,966,988; and *Tetrahedron Letters* (2004) 45: 8355, footnote 12.

The present invention relates to the solid state physical properties of Cinacalcet hydrochloride. These properties can be influenced by controlling the conditions under which Cinacalcet hydrochloride is obtained in solid form. Solid state physical properties include, for example, the flowability of the milled solid, the rate of dissolution in an aqueous fluid, behavior on compaction, and storage stability. The discovery of new processes of preparing such polymorphic forms provides opportunities to improve the performance characteristics of a pharmaceutical product.

The FDA's published Summary Basis of Approval of New Drug Application #21688 mentions that Cinacalcet hydrochloride has only one stable crystalline form at ambient temperature. However, there is no prior art disclosure of a process for preparing crystalline cinacalcet hydrochloride. Therefore, there is a need in the art for additional processes for the preparation of crystalline cinacalcet hydrochloride.

SUMMARY OF THE INVENTION

The present invention is directed to processes for the preparation of a cinacalcet hydrochloride crystalline form (denominated Form I) characterized by powder X-ray diffraction peaks at about 13.9, 19.0, 21.3, and 25.5±0.2 degrees 2θ.

In another embodiment, the present invention encompasses a method of preparing cinacalcet hydrochloride crystalline Form I comprising providing a solution of cinacalcet base in a solvent in which cinacalcet hydrochloride has a low solubility; acidifying the solution with hydrochloric acid to obtain a reaction mixture; maintaining the reaction mixture to obtain a precipitate; and recovering the precipitated cinacalcet hydrochloride crystalline Form I.

In one embodiment of the present invention, the present invention encompasses a method of preparing cinacalcet hydrochloride crystalline Form I comprising providing a slurry of amorphous cinacalcet hydrochloride, in a solvent selected from the group consisting of water, MTBE and $C_5$-$C_8$ alkanes; maintaining the slurry at a temperature of from about room temperature to reflux temperature for about 2 to 30 hours; and recovering cinacalcet hydrochloride crystalline Form I.

In another embodiment, the present invention encompasses a method of preparing cinacalcet hydrochloride crystalline Form I comprising providing a solution of cinacalcet hydrochloride in a solvent selected from a $C_{3-6}$ ketone or $C_1$-$C_5$ straight or branched alcohol; combining the solution with an anti-solvent; maintaining the solution to obtain a precipitate; and recovering cinacalcet hydrochloride crystalline form I.

DETAILED DESCRIPTION OF THE INVENTION

As used herein, "RT" refers to room temperature and is meant to indicate a temperature of about 18° to about 25° C., preferably about 20° to about 22° C.

As used herein, "cinacalcet hydrochloride crystalline Form I" refers to a crystalline form of cinacalcet hydrochloride characterized by powder X-ray diffraction ("XRD") peaks at about 13.9, 19.0, 21.3, and 25.5±0.2 degrees 2θ.

Figure 4:
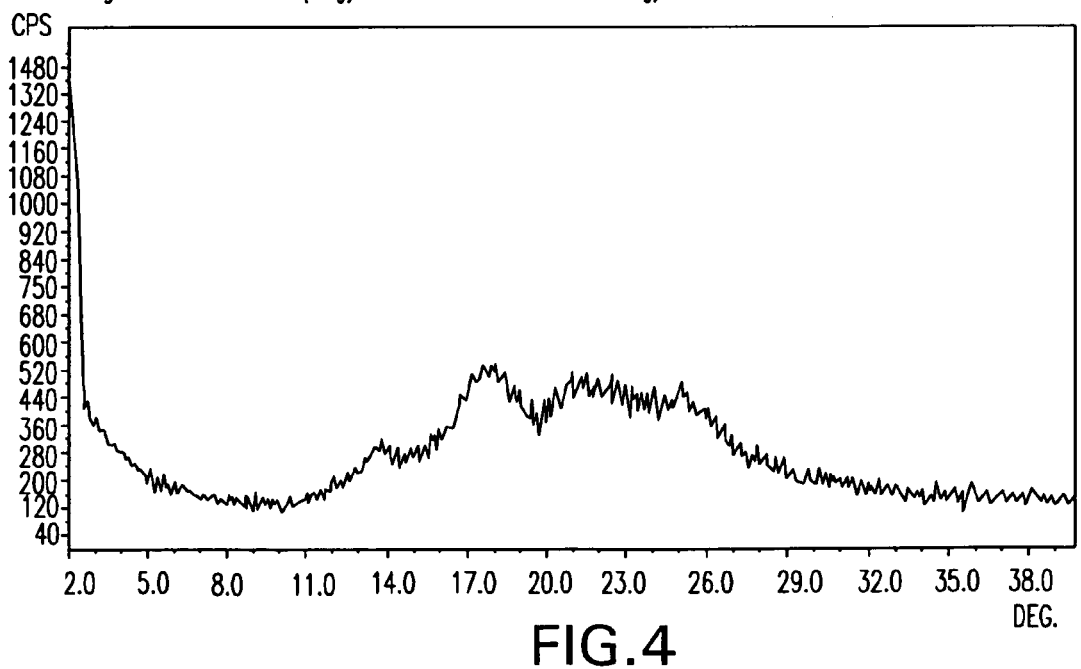
FIG. 4 illustrates an X-Ray Powder Diffraction pattern of amorphous cinacalcet hydrochloride.

As used herein, "amorphous cinacalcet hydrochloride" refers to a form of cinacalcet hydrochloride that is characterized by a powder XRD pattern substantially as depicted in FIG. 4 and that can be prepared by the processes disclosed in co-pending U.S. provisional application Nos. 60/739,215 and 60/742,626.

Figure 1:
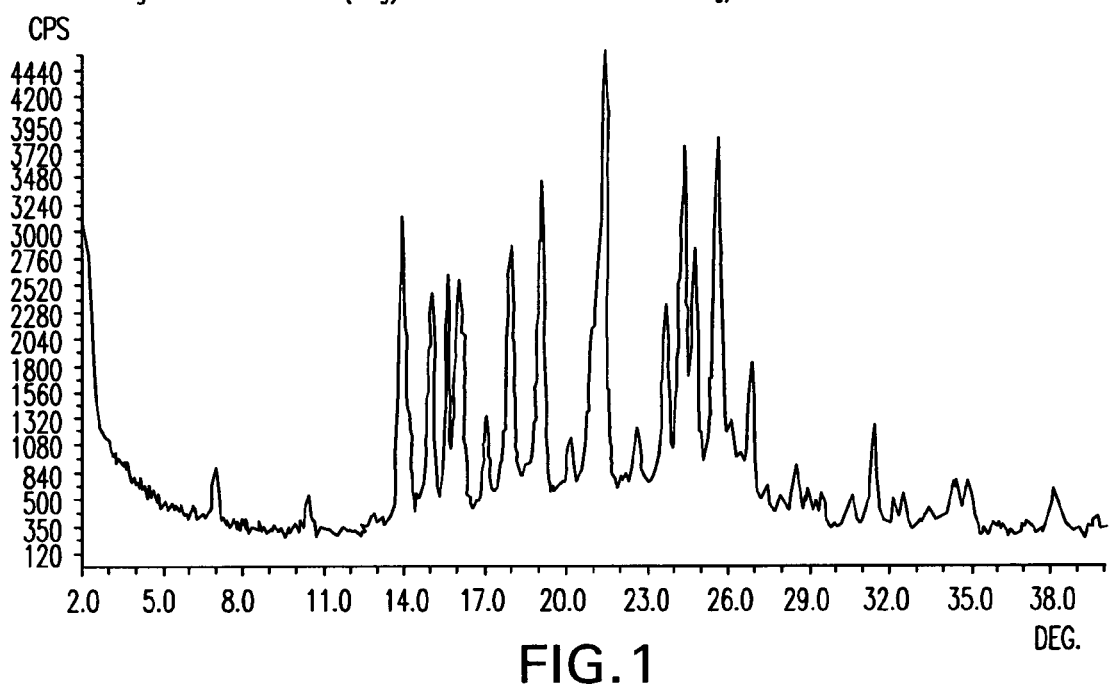
FIG. 1 illustrates an XRD diffractogram of cinacalcet hydrochloride crystalline Form I.
Figure 3:
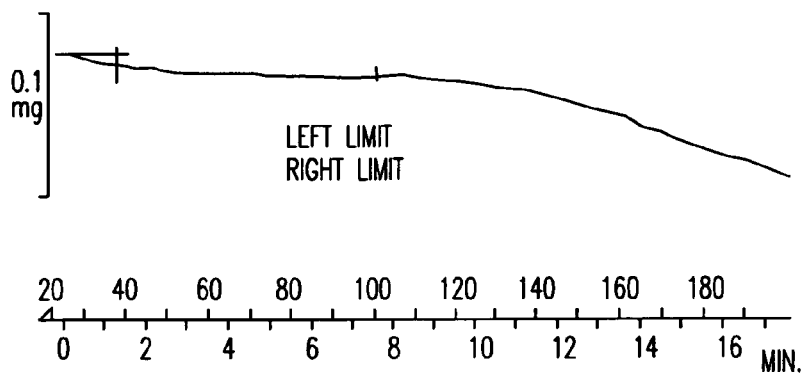
FIG. 3 illustrates a TGA thermogram of cinacalcet hydrochloride crystalline Form I.

The crystalline cinacalcet hydrochloride currently marketed as SENSIPAR™ is characterized by powder XRD peaks at about 13.9, 19.0, 21.3, and 25.5±0.2 degrees 2θ. This crystalline form may be further characterized by a powder XRD pattern with peaks at about 15.0, 15.5, 16.0, 17.9, 23.7, and 24.3±0.2 degrees 2θ or substantially as depicted in FIG. 1. Differential Scanning Calorimetry ("DSC") thermogram of the crystalline form shows two endothermic peaks at about 160° C. to about 170° C. and at about 175° C. to about 185° C., substantially as depicted in FIG. 3. The Thermogravimetic Analysis ("TGA") thermogram of this crystalline form, substantially as depicted in FIG. 4, shows weight loss of less than 1%, thus this form may be considered anhydrous.

In another embodiment, the present invention encompasses a method of preparing cinacalcet hydrochloride crystalline form I comprising providing a solution of cinacalcet base in a solvent in which cinacalcet hydrochloride has a low solubility; acidifying the solution with hydrochloric acid to obtain a reaction mixture; maintaining the reaction mixture to obtain a precipitate; and recovering the precipitated cinacalcet hydrochloride crystalline Form I.

Solvents in which cinacalcet hydrochloride has a low solubility include, but are not limited to water, a $C_3$-$C_6$ ketone, a $C_5$-$C_8$ aliphatic or aromatic hydrocarbon, a $C_3$-$C_6$ ester other than ethyl acetate, a $C_1$-$C_5$ alcohol, $C_2$-$C_5$ ether, dimethylacetamide ("DMAc"), dimethylformamide ("DMF"), dimethylsulfoxide ("DMSO"), N-methyl-2-pyrrolidone ("NMP"), and mixtures thereof. Preferably, the solvent is selected from a group consisting of water, acetone, n-heptane, n-pentane, diethyl ether, isobutyl acetate, toluene, methyl tert-butyl ether ("MTBE"), ethanol, DMF, DMSO, NMP, acetonitrile, DMA, DMAc, n-pentane, n-hexane and cyclohexane. More preferably the solvent is selected from a group consisting of water, toluene, acetone, and MTBE. Most preferably, the solvent is MTBE.

Cinacalcet base and solvent are combined at about room temperature in at least an amount sufficient to obtain a solution.

Acidifying the mixture can be either with gaseous or aqueous hydrochloric acid. Preferably, when the solution is acidified with aqueous hydrochloric acid, the acid is in an amount sufficient to react with substantially all of the cinacalcet base, more preferably an amount from about 1 to about 2 moles per mole of cinacalcet base. The aqueous solution may be added drop-wise or in one portion. Preferably, when the solution is acidified with gaseous hydrochloric acid, it is acidified until there is no more precipitate formed.

Preferably, the reaction mixture obtained after the addition of hydrochloric acid is stirred for about 20 minutes to about 72 hours.

Cinacalcet hydrochloride crystalline form I may be recovered by any method known in the art, such as by filtering, washing, preferably with the solvent used, and drying. Drying is preferably performed until a constant weight is obtained, preferably at a temperature of from about 45° C. to about 55° C., most preferably at a temperature of about 50° C., under reduced pressure.

In one embodiment of the present invention, cinacalcet crystalline Form I is prepared in a process comprising providing a slurry of amorphous cinacalcet hydrochloride, in a solvent selected from the group consisting of water, MTBE, and $C_5$-$C_8$ alkanes; maintaining the slurry at a temperature of from about room temperature to reflux temperature for about 2 to 30 hours; and recovering cinacalcet hydrochloride crystalline Form I.

Preferably, the solvent is selected from the group consisting of water, MTBE, and n-hexane. Preferably, the solvent is used in an amount of from about 5 to about 25 ml per gram of the amorphous cinacalcet hydrochloride.

Preferably, maintain the slurry is for at least about 2 hours, more preferably from about 2 to about 24 hours.

The recovering step may comprise filtering, washing and drying. Drying is preferably performed under reduced pressure, preferably a vacuum, at a temperature of from about 40° to about 60° C., more preferably from about 45° to about 50° C. Preferably, the product is dried for at least about 5 hours, and, more preferably, from about 7 to about 24 hours.

In another embodiment, the present invention encompasses a method of preparing cinacalcet hydrochloride crystalline form I comprising providing a solution of cinacalcet hydrochloride in a solvent selected from a $C_{3-6}$ ketone or $C_1$-$C_5$ straight or branched alcohol; combining the solution with an anti-solvent; maintaining the solution to obtain a precipitate; and recovering cinacalcet hydrochloride crystalline Form I.

Preferably, the solvent is selected from the group consisting of acetone, ethanol, isopropyl alcohol ("IPA"), and methanol. Preferably, the solvent is in at least an amount sufficient to obtain a solution, preferably, in amount of from about 3 to about 33 ml per gram of cinacalcet hydrochloride.

The anti-solvent is a solvent in which cinacalcet hydrochloride has a low solubility. Preferably, the anti-solvent is selected from the group consisting of water, a cyclic or non-cyclic $C_5$-$C_8$ hydrocarbon, aliphatic or branched $C_2$-$C_5$ ethers, and mixtures thereof. More preferably, the anti-solvent is a solvent in which cinacalcet hydrochloride is substantially insoluble, such as water, n-heptane, n-hexane, n-pentane, diethyl ether, MTBE, cyclohexane, or mixtures thereof.

Combining the solution with the anti-solvent can be accomplished either in one portion or drop-wise. The anti-solvent is preferably added in an amount of from about 4 volumes to about 100 volumes of solution. The reaction mixture obtained after the addition of the anti-solvent is preferably stirred for at least about 10 minutes, more preferably from about 10 minutes to about 24 hours.

Cinacalcet hydrochloride crystalline Form I may be recovered by any method known in the art, such as by filtering, washing, preferably with the solvent used, and drying. Drying is preferably performed until a constant weight is obtained, preferably at a temperature of from about 45° C. to about 55° C., more preferably at a temperature of about 50° C., under reduced pressure.

Having described the invention with reference to certain preferred embodiments, other embodiments will become apparent to one skilled in the art from consideration of the specification.

The invention is further defined by reference to the following examples describing in detail the methods of preparation of the invention. It will be apparent to those skilled in the art that many modifications, both to materials and methods, may be practiced without departing from the scope of the invention.

EXAMPLES

Preparation of Cinacalcet Hydrochloride Crystalline Form I from Amorphous Cinacalcet Hydrochloride Example 1

A slurry of 0.5 gram of amorphous cinacalcet hydrochloride in 4 ml of water was stirred at reflux temperature for 23.5 hours, and then cooled to room temperature. The product was isolated by filtration, washed with 2 ml of water, and dried at 50° C. in a vacuum oven for 23 hours, providing 0.43 gram of cinacalcet hydrochloride crystalline Form I.

Example 2

A slurry of 0.3 gram of amorphous cinacalcet hydrochloride in 4 ml of MTBE was stirred at room temperature for 18.5 hours. The product was then isolated by filtration, washed with 2 ml of MTBE, and dried at 50° C. in a vacuum oven for 7 hours, providing 0.26 gram of cinacalcet hydrochloride crystalline Form I.

Example 3

A slurry of 0.3 gram of amorphous cinacalcet hydrochloride in 6 ml of MTBE was stirred at reflux temperature for 2 hours, cooled to room temperature, and then stirred at room temperature for an additional 16 hours. The product was isolated by filtration, washed with 4 ml of MTBE, and dried at 50° C. in a vacuum oven for 7 hours, providing 0.19 gram of cinacalcet hydrochloride crystalline Form I.

Example 4

A slurry of 0.3 gram of amorphous cinacalcet hydrochloride in 6 ml of n-hexane was stirred at reflux temperature for 4 hours, and then cooled to room temperature. The product was isolated by filtration, washed with 5 ml of n-hexane, and dried at 45° C. in a vacuum oven for 15 hours, providing 0.23 gram of cinacalcet hydrochloride crystalline Form I.

Preparation of Cinacalcet Hydrochloride Crystalline Form I from Cinacalcet Base

Example 5

Figure 2:
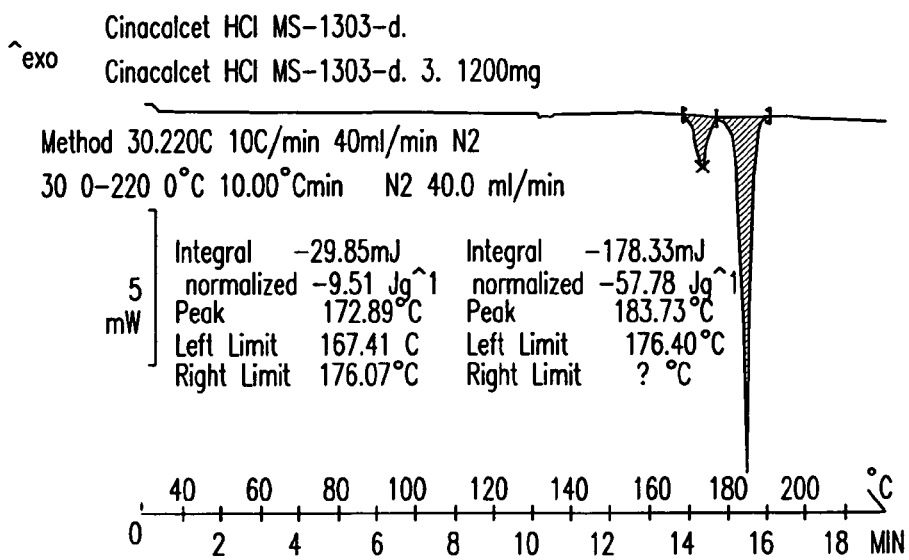
FIG. 2 illustrates a DSC thermogram of cinacalcet hydrochloride crystalline Form I.

A solution of cinacalcet base was formed by dissolving 1.0 g of cinacalcet base in 4 ml of absolute ethanol. Then, 15 ml of 1N hydrochloric acid ("HCl") was added drop-wise to the solution. The resulting mixture was stirred at ambient temperature for 20 hours, producing a precipitate. The product was isolated by filtration, washed with 6 ml of water, and dried in a vacuum oven at 50° C. for 24 hours, yielding 0.97 g of cinacalcet hydrochloride. The final product was analyzed by powder XRD. The resulting powder XRD diffractogram illustrated in FIG. 2, shows the product to be cinacalcet hydrochloride crystalline Form I.

Example 6

0.93 g of cinacalcet base was dissolved in 50 ml of n-heptane at room temperature. Then, HCl gas was bubbled into the solution, producing a precipitate. The HCl gas was added until no more precipitation was observed. The resulting slurry was then stirred at room temperature for 0.5 hour. The product was isolated by filtration, washed with 10 ml of n-heptane, and dried at 50° C. in a vacuum oven for 17 hours, yielding 0.75 g of cinacalcet hydrochloride crystalline Form I.

Example 7

0.3 g of cinacalcet base was stirred in 6 ml of n-heptane at room temperature. Then, 3 ml of 1N HCl were added in one portion, resulting in an immediate precipitation. The resulting mixture was stirred at room temperature, i.e., about 20° to about 25° C., overnight. The product was isolated by filtration, washed with 4 ml of n-heptane, and dried at 50° C. in a vacuum oven for 25 hours, yielding 0.3 g of cinacalcet hydrochloride crystalline Form I.

Example 8

0.8 g of cinacalcet base was dissolved in 50 ml of n-hexane at room temperature. Then, HCl gas was bubbled into the solution, producing a precipitate. The HCl gas was added until no more precipitation was observed. The resulting slurry was stirred at room temperature for 20 minutes. The product was isolated by filtration, washed with 10 ml of n-Hexane, and dried at 50° C. in a vacuum oven for 17 hours, yielding 0.76 g of cinacalcet hydrochloride crystalline Form I.

Example 9

0.85 g of cinacalcet base was dissolved in 50 ml of cyclohexane at room temperature. Then, HCl gas was bubbled into the solution until an oily precipitate was obtained. The mixture was then stirred at room temperature for 16 hours. The product was isolated by filtration and dried at 50° C. in a vacuum oven for 24 hours, yielding 0.54 g of cinacalcet hydrochloride crystalline Form I.

Example 10

0.75 g of cinacalcet base was dissolved in 50 ml of diethyl ether at room temperature. Then, HCl gas was bubbled into the solution to obtain a precipitate. The resulting slurry was stirred at room temperature for 20 minutes. The product was then isolated by filtration, washed with 10 ml of diethyl ether, and dried at 50° C. in a vacuum oven for 16 hours, yielding 0.55 g of cinacalcet hydrochloride crystalline Form I.

Example 11

0.3 g of cinacalcet base was dissolved in 6 ml of diethyl ether at room temperature, i.e., about 20° to about 25° C. Then, 3 ml of 1N HCl were added to the solution in one portion, resulting in an immediate precipitation. The resulting slurry was stirred at room temperature, i.e., about 20° to about 25° C., overnight. The product was isolated by filtration, washed with 5 ml of diethyl ether, and dried at 50° C. in a vacuum oven for 24 hours, yielding 0.26 g of cinacalcet hydrochloride crystalline Form I.

Example 12

0.72 g of cinacalcet base was stirred in 50 ml of water at room temperature. Then, HCl gas was bubbled into the solution to obtain a precipitate. The resulting slurry was stirred at room temperature for 2.5 hours. The product was isolated by filtration, washed with 20 ml of water, and dried at 50° C. in a vacuum oven for 19 hours, yielding 0.56 g of cinacalcet hydrochloride crystalline Form I.

Example 13

1.0 g of cinacalcet base was partially dissolved in 30 ml of n-pentane at room temperature. Then, HCl gas was bubbled into the solution, producing a precipitate. The HCl gas was added until no more precipitation was observed. The resulting slurry was stirred at room temperature for 0.5 hour. The product was isolated by filtration, washed twice with 25 ml of n-pentane, and dried at 50° C. in a vacuum oven for 16 hours, yielding 0.87 g of cinacalcet hydrochloride crystalline Form I.

Example 14

2.2 grams of cinacalcet base was dissolved in 2 ml of acetone at room temperature. Then, 10 ml of 1N HCl was added in one portion and the mixture was stirred at room temperature for 1 hour, yielding a precipitate. The product was isolated by filtration, washed with 10 ml of water, and dried at 50° C. in a vacuum oven for 24 hours, providing 1.75 grams of cinacalcet hydrochloride crystalline Form I. Purity: 99.9 HPLC area percent.

Example 15

2.0 grams of cinacalcet base was dissolved in acetone (10 ml). Then HCl gas (0.3 g; 1.5 eq.) was bubbled into the solution. The obtained solution was evaporated under reduced pressure until dryness to obtain 2.1 g of cinacalcet hydrochloride crystalline Form I.

Example 16

Cinacalcet base (2.0 g) was dissolved in acetone (4 ml) at room temperature. Then 1N HCl (1.5 eq.) and water (40 ml) were added to the solution. The resulting mixture was stirred at room temperature for 4 hours to obtain a precipitate. The product was isolated by filtration, washed with water (10 ml) and dried at 50° C. in a vacuum oven for 24 hours to obtain 1.75 g of cinacalcet hydrochloride crystalline Form I.

Example 17

0.3 g of cinacalcet base was dissolved in 4 ml of isobutyl acetate at room temperature, i.e., about 20° to about 25° C. Then, 2 ml of 1N HCl were added in one portion, and the mixture was stirred at room temperature overnight, yielding a precipitate. The product was isolated by filtration, washed with 5 ml of isobutyl acetate, and dried at 50° C. in a vacuum oven for 24 hours, yielding 0.12 g of cinacalcet hydrochloride crystalline Form I.

Example 18

0.49 g cinacalcet base was dissolved in 10 ml of toluene at room temperature, i.e., about 20° to about 25° C. Then, 2 ml of 1N HCl was added in one portion, and the resulting mixture was stirred at room temperature overnight, yielding a precipitate. The product was isolated by filtration, washed with 10 ml of toluene, and dried at 50° C. in a vacuum oven for 17 hours, yielding 0.02 g of cinacalcet hydrochloride crystalline Form I.

Example 19

1.2 g of cinacalcet base was stirred in 20 ml of MTBE at room temperature. Then, 10 ml of 1N HCl was added in one portion. Precipitation occurred immediately. The mixture was stirred at room temperature for 4 hours. The product was isolated by filtration, washed with 5 ml of MTBE, and dried at 50° C. in a vacuum oven for 16.5 hours, yielding 0.58 g of cinacalcet hydrochloride crystalline Form I.

Example 20

0.83 g of cinacalcet base was dissolved in 50 ml of MTBE at room temperature. Then HCl gas was bubbled into the solution. The solution was stirred at room temperature for 0.5 hour to obtain precipitate. The product was isolated by filtration, washed with 8 ml of MTBE, and dried at 50° C. in a vacuum oven for 15 hours, yielding 0.5 g of cinacalcet hydrochloride crystalline Form I.

Example 21

CNC base (3.15 g) was dissolved in MTBE (15 vol.) at room temperature. HCl gas was bubbled into the obtained solution, producing a precipitate. The HCl gas was added until no more precipitation was observed. The slurry was stirred at room temperature for additional 1 hour. The product was then isolated by filtration, washed with MTBE (2×2 ml) and dried in a vacuum oven at 50° C. for 16 hours to obtain 1.93 g of cinacalcet hydrochloride crystalline Form I.

Example 22

CNC base (3.0 g) was dissolved in MTBE (20 vol.) at room temperature. HCl gas was bubbled into the obtained solution, producing a precipitate. The HCl gas was added until no more precipitation was observed. The slurry was stirred at room temperature for additional 1 hour. The product was then isolated by filtration, washed with MTBE (2×2 ml) and dried in a vacuum oven at 50° C. for 15 hours to obtain 2.08 g of cinacalcet hydrochloride crystalline Form I.

Example 23

0.75 g of cinacalcet base was dissolved in 3 ml of absolute ethanol at room temperature. Then, 14 ml of 1N HCl was added drop-wise to the solution and the resulting mixture was stirred at room temperature for 3.5 hours to obtain a precipitate. The product was isolated by filtration, washed with 2 ml of water, and dried at 50° C. in a vacuum oven for 17 hours, yielding 0.5 g of cinacalcet hydrochloride crystalline Form I.

Example 24

5 g of CNC base were dissolved in 5 ml DMF at room temperature. Then 50 ml of 1N HCl were added drop-wise to the solution over a period of 4 minutes. The resulting slurry was stirred at room temperature for 3 hrs. The product was isolated by vacuum filtration, washed with 2×10 ml of water, and dried at 50° C. for 14.5 hours to obtain 4.13 g of cinacalcet hydrochloride crystalline Form I.

Example 25

5 g of CNC base were dissolved in 5 ml DMSO at room temperature. Then 50 ml of 1N HCl were added drop-wise to the solution over a period of 10 minutes. The resulting slurry was stirred at room temperature for 3 hrs. The product was isolated by vacuum filtration, washed with 2×15 ml of water, and dried at 50° C. for 14.5 hours to obtain 4.11 g of cinacalcet hydrochloride crystalline Form I.

Example 26

5 g of CNC base were dissolved in 5 ml NMP at room temperature. Then 50 ml of 1N HCl were added drop-wise over a period of 8 minutes. The resulting slurry was stirred at room temperature for 3 hrs. The product was isolated by vacuum filtration, washed with 2×10 ml of water, and dried at 50° C. for 14.5 hours to obtain 4.31 g of cinacalcet hydrochloride crystalline Form I.

Example 27

5 g of CNC base were dissolved in 5 ml acetonitrile at room temperature. Then 50 ml of 1N HCl were added drop-wise over a period of 7 minutes. The resulting slurry was stirred at room temperature for 5 hrs. The product was isolated by vacuum filtration, washed with 2×10 ml of water, and dried at 50° C. for 14.5 hours to obtain 4.30 g of cinacalcet hydrochloride crystalline Form I.

Example 28

5 g of CNC base were dissolved in 5 ml dimethylacetamide at room temperature. Then 50 ml of 1N HCl were added drop-wise to the solution over a period of 12 minutes. The resulting slurry was stirred at room temperature for 4 hrs. The product was isolated by vacuum filtration, washed with 2×10 ml of water, and dried at 50° C. for 14.5 hours to obtain 4.53 g of cinacalcet hydrochloride crystalline Form I.

Preparation of Cinacalcet Hydrochloride Crystalline Form I from Cinacalcet Hydrochloride by Solvent/Antisolvent Method Example 29

0.3 g of cinacalcet hydrochloride was dissolved in 7 ml of acetone at room temperature. Then, 35 ml of n-heptane was added in one portion and the mixture was stirred at room temperature for 16 hours. The product was isolated by filtration, washed with 4 ml of n-heptane and dried at 50° C. in a vacuum oven for 23 hours, yielding 0.26 g of cinacalcet hydrochloride crystalline Form I.

Example 30

0.3 g of cinacalcet hydrochloride was dissolved in 9 ml of acetone at room temperature. Then, 45 ml of diethyl ether was added in one portion and the mixture was stirred at room temperature for 16 hours. The product was isolated by filtration and dried at 50° C. in a vacuum oven for 23 hours, yielding 0.18 g of cinacalcet hydrochloride crystalline Form I.

Example 31

1.0 g of cinacalcet hydrochloride was dissolved in 18 ml of acetone at room temperature. The obtained solution was added drop-wise to 300 ml of diethyl ether and the mixture was stirred at room temperature for 2 hours. The product was isolated by filtration and dried at 50° C. in a vacuum oven for 16 hours, yielding 0.53 g of cinacalcet hydrochloride crystalline Form I.

Example 32

0.3 g of cinacalcet hydrochloride was dissolved in 9 ml of acetone at room temperature. Then, 50 ml of n-hexane was added in one portion and the mixture was stirred at room temperature for 5 hours. The product was isolated by filtration, washed with 2 ml of n-hexane and dried at 50° C. in a vacuum oven for 16 hours, yielding 0.3 g of cinacalcet hydrochloride crystalline Form I.

Example 33

0.3 g of cinacalcet hydrochloride was dissolved in 9 ml of acetone at room temperature. Then, 70 ml of MTBE was added in one portion and the mixture was stirred at room temperature for 16 hours. The product was isolated by filtration and dried at 50° C. in a vacuum oven for 24 hours, yielding 0.16 g of cinacalcet hydrochloride crystalline Form I.

Example 34

0.3 g of cinacalcet hydrochloride was dissolved in 7 ml of acetone at room temperature. Then, 50 ml of cyclohexane was added in one portion and the mixture was stirred at room temperature for 4 hours. The product was isolated by filtration, washed with 4 ml of cyclohexane and dried at 50° C. in a vacuum oven for 16 hours, yielding 0.23 g of cinacalcet hydrochloride crystalline Form I.

Example 35

0.3 g of cinacalcet hydrochloride was dissolved in 9 ml of acetone at room temperature. Then, 50 ml of n-pentane was added in one portion and the mixture was stirred at room temperature for 4 hours. The product was isolated by filtration, washed with 3 ml of n-pentane and dried at 50° C. in a vacuum oven for 16 hours, yielding 0.35 g of cinacalcet hydrochloride crystalline Form I.

Example 36

0.3 g of cinacalcet hydrochloride was dissolved in 2 ml of absolute ethanol at room temperature. Then, 15 ml of n-pentane was added drop-wise and the mixture was stirred at room temperature for 2.5 hours. The product was isolated by filtration, washed with 2 ml of n-pentane and dried at 50° C. in a vacuum oven for 18 hours, yielding 0.24 g of cinacalcet hydrochloride crystalline Form I.

Example 37

0.5 g of cinacalcet hydrochloride was dissolved in 3 ml of absolute ethanol at room temperature. The obtained solution was added drop-wise to 300 ml of n-pentane and the mixture was stirred at room temperature for 10 minutes. The product was isolated by filtration and dried at 50° C. in a vacuum oven for 17.5 hours, yielding 0.3 g of cinacalcet hydrochloride crystalline Form I.

Example 38

0.3 g of cinacalcet hydrochloride was dissolved in 2 ml of absolute ethanol at room temperature. Then, 15 ml of n-pentane was added drop-wise and the mixture was stirred at room temperature for 3 hours. The product was isolated by filtration, washed with 2 ml of n-pentane and dried at 50° C. in a vacuum oven for 18 hours, yielding 0.18 g of cinacalcet hydrochloride crystalline Form I.

Example 39

0.3 g of cinacalcet hydrochloride was dissolved in 2 ml of absolute ethanol at room temperature. Then, 15 ml of MTBE was added drop-wise and the mixture was stirred at room temperature for 3 hours. The product was isolated by filtration and dried at 50° C. in a vacuum oven for 18 hours, yielding 0.16 g of cinacalcet hydrochloride crystalline Form I.

Example 40

0.3 g of cinacalcet hydrochloride was dissolved in 2 ml of absolute ethanol at room temperature. Then, 15 ml of water was added drop-wise and the mixture was stirred at room temperature for 3.5 hours. The product was isolated by filtration, washed with 5 ml of water and dried at 50° C. in a vacuum oven for 18 hours, yielding 0.19 g of cinacalcet hydrochloride crystalline Form I.

Example 41

0.3 g of cinacalcet hydrochloride was dissolved in 2 ml of absolute ethanol at room temperature. Then, 15 ml of diethyl ether was added drop-wise and the mixture was stirred at room temperature for 16 hours. The product was isolated by filtration and dried at 50° C. in a vacuum oven for 17 hours, yielding 0.14 g of cinacalcet hydrochloride crystalline Form I.

Example 42

0.24 g of cinacalcet hydrochloride was dissolved in 1.5 ml of absolute ethanol at room temperature. Then, 15 ml of n-hexane was added drop-wise and the mixture was stirred at room temperature for 16 hours. The product was isolated by filtration and dried at 50° C. in a vacuum oven for 17 hours, yielding 0.23 g of cinacalcet hydrochloride crystalline Form I.

Example 43

0.4 g of cinacalcet hydrochloride was dissolved in 13 ml of IPA at room temperature. Then, 50 ml of n-Hexane was added in one portion and the mixture was stirred at room temperature for 6.5 hours. The product was isolated by filtration and dried at 50° C. in a vacuum oven for 16 hours, yielding 0.05 g of cinacalcet hydrochloride crystalline Form I.

Example 44

0.3 g of cinacalcet hydrochloride was dissolved in 10 ml of IPA at room temperature. Then, 50 ml of n-pentane was added in one portion and the mixture was stirred at room temperature for 2.5 hours. The product was isolated by filtration and dried at 50° C. in a vacuum oven for 17.5 hours, yielding 0.1 g of cinacalcet hydrochloride crystalline Form I.

Example 45

0.64 g of cinacalcet hydrochloride was dissolved in 2 ml of methanol at room temperature. Then, 15 ml of water was added in one portion and the mixture was stirred at room temperature for 50 minutes. The product was isolated by filtration and dried at 50° C. in a vacuum oven for 17 hours, yielding 0.4 g of cinacalcet hydrochloride crystalline Form I.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed is:

1. A process for preparing a crystalline form of Cinacalcet hydrochloride, wherein the crystalline form of Cinacalcet hydrochloride is characterized by powder XRD peaks at about 13.9, 19.0, 21.3, 25.5±0.2° 2θ, the process comprising:
  a. providing a solution of Cinacalcet base in a solvent in which Cinacalcet hydrochloride has a low solubility;
  b. acidifying the solution with hydrochloric acid to obtain a reaction mixture;
  c. maintaining the reaction mixture to obtain a precipitate; and
  d. recovering precipitated Cinacalcet hydrochloride crystal form I.

2. The process of claim 1, wherein the solvent is selected from the group consisting of water, a $C_3$-$C_6$ ketone, a $C_5$-$C_8$ aliphatic or aromatic hydrocarbon, a $C_3$-$C_6$ ester other than ethyl acetate, a $C_2$-$C_5$ alcohol, a $C_2$-$C_5$ ether, DMAc, DMF, DMSO, NMP, and mixtures thereof.

3. The process of claim 2, wherein the solvent is selected from the group consisting of water, acetone, n-heptane, n-pentane, diethyl ether, isobutyl acetate, toluene, MTBE, ethanol, DMF, DMSO, NMP, acetonitrile, DMA, n-pentane, n-hexane, and cyclohexane.

4. The process of claim 3, wherein the solvent is selected from the group consisting of water, toluene, acetone, and MTBE.

5. The process of claim 1, wherein the hydrochloric acid is gaseous or aqueous.

6. The process of claim 5, further comprising acidifying the solution with gaseous hydrochloric acid until no additional precipitate is formed.

7. The process of claim 1, further comprising maintaining the reaction mixture for about 20 minutes to about 72 hours.

8. The process of claim 1, further comprising filtering, washing, and drying the precipitate to recover the Cinacalcet hydrochloride.

9. The process of claim 8, further comprising drying the precipitate at a temperature of from about 45° C. to about 55° C. under reduced pressure.

10. A process for preparing a crystalline form of Cinacalcet hydrochloride, wherein the Cinacalcet hydrochloride is characterized by powder XRD peaks at about 13.9, 19.0, 21.3, 25.5±0.2° 2θ, the process comprising:
   a. providing a slurry of amorphous Cinacalcet hydrochloride, characterized by an XRD diffractogram, substantially as depicted in FIG. 4, in a solvent selected from the group consisting of water, MTBE, and $C_5$-$C_8$ alkanes;
   b. maintaining the slurry at a temperature of from about room temperature to reflux temperature for about 2 to 30 hours; and
   c. recovering Cinacalcet hydrochloride crystal Form I.

11. The process of claim 10, wherein the solvent is water, MTBE, or n-hexane.

12. The process of claim 10, wherein the solvent is used in an amount of from about 5 to about 25 ml per gram of the Cinacalcet hydrochloride form I.

13. The process of claim 10, wherein the slurry is maintained for at least about 2 hours.

14. The process of claim 13, wherein, the slurry is maintained for about 2 to about 24 hours.

15. The process of claim 10, further comprising filtering, washing, and drying the slurry to recover the Cinacalcet hydrochloride.

16. The process of claim 15, further comprising drying the filtered and washed slurry under a reduced pressure, at a temperature of from about 40° to about 60° C.

17. The process of claim 16, further comprising drying the filtered and washed slurry at a temperature of from about 45° to about 50° C.

18. The process of claim 15, further comprising drying the filtered and washed slurry for at least about 5 hours.

19. The process of claim 15, further comprising drying the filtered and washed slurry for about 7 to about 24 hours.

20. A process for preparing Cinacalcet hydrochloride crystalline form I comprising:
   a. providing a solution of Cinacalcet hydrochloride in a solvent selected from a $C_{3-6}$ ketone, $C_1$-$C_5$ straight or branched alcohol, and mixtures thereof;
   b. combining the solution with an antisolvent;
   c. maintaining the solution to obtain a precipitate; and
   d. recovering Cinacalcet hydrochloride crystal form I.

21. The process of claim 20, wherein the solvent is selected from the group consisting of acetone, ethanol, IPA, and methanol.

22. The process of claim 20, wherein the antisolvent is one in which Cinacalcet hydrochloride is substantially insoluble.

23. The process of claim 20, wherein the antisolvent is selected from the group consisting of water, a cyclic or non-cyclic $C_5$-$C_8$ hydrocarbon, an aliphatic or branched $C_2$-$C_5$ ether, and mixtures thereof.

24. The process of claim 20, wherein the antisolvent is selected from the group consisting of water, n-heptane, n-hexane, n-pentane, diethyl ether, MTBE, cyclohexane, and mixtures thereof.

25. The process of claim 20, wherein the antisolvent is added in an amount of from about 4 volumes to about 100 volumes of solution.

26. The process of claim 20, further comprising maintaining the solution to obtain a precipitate by stirring for at least about 10 minutes.

27. The process of claim 20, further comprising maintaining the solution to obtain a precipitate by stirring for about 10 minutes to about 24 hours.

28. The process of claim 20, further comprising filtering, washing, and drying the precipitate to recover the Cinacalcet hydrochloride.

29. The process of claim 20, further comprising drying the precipitate at a temperature of from about 45° C. to about 55° C. under reduced pressure.

* * * * *

UNITED STATES PATENT AND TRADEMARK OFFICE
CERTIFICATE OF CORRECTION

PATENT NO.        : 7,247,751 B2
APPLICATION NO.   : 11/439570
DATED             : July 24, 2007
INVENTOR(S)       : Lifshitz-Liron et al.

It is certified that error appears in the above-identified patent and that said Letters Patent is hereby corrected as shown below:

Column 3, line 66, change "DMA, DMAc" to --DMAc--

Column 12, line 66, change "DMA" to --DMAc--

Signed and Sealed this

Ninth Day of June, 2009

JOHN DOLL
*Acting Director of the United States Patent and Trademark Office*